United States Patent [19]
Mackey

[11] Patent Number: 5,423,877
[45] Date of Patent: Jun. 13, 1995

[54] METHOD AND DEVICE FOR ACUTE PAIN MANAGEMENT BY SIMULTANEOUS SPINAL CORD ELECTRICAL STIMULATION AND DRUG INFUSION

[75] Inventor: David C. Mackey, 323 Green Castle Dr., Jacksonville, Fla. 32225

[73] Assignees: David C. Mackey; Jill Mackey, both of Jacksonville, Fla.

[21] Appl. No.: 878,436

[22] Filed: May 4, 1992

[51] Int. Cl.⁶ ............................................. A61N 1/04
[52] U.S. Cl. .................................. 607/117; 607/116; 128/642; 128/898
[58] Field of Search .................. 128/642, 783–786, 128/898, 639, 804; 604/20, 21, 48, 49; 606/32, 33, 41

[56] References Cited

U.S. PATENT DOCUMENTS

| | | | |
|---|---|---|---|
| 4,633,889 | 1/1987 | Talalla et al. | 128/784 |
| 5,081,990 | 1/1992 | Deletis | 128/784 |

FOREIGN PATENT DOCUMENTS 9207605  5/1992  WIPO ................................ 128/642

Primary Examiner—Stephen C. Pellegrino
Assistant Examiner—Michael Peffley
Attorney, Agent, or Firm—Thomas C. Saitta

[57] ABSTRACT

A multi-lead electrode catheter for use in acute pain management and a method utilizing this device is provided. The electrode catheter has a plurality of longitudinally spaced electrodes, and a conduit for infusion of analgesic medications simultaneous with application of electrical stimulation to the epidural space of the spinal cord, such that three to four dermatome and myotome body regions are affected. The device is properly positioned without the aid of fluoroscopy in response to communication from the patient as to which dermatomes and myotomes are experiencing paresthesias caused by the electrical stimulation of the corresponding nerve fibers.

2 Claims, 1 Drawing Sheet

METHOD AND DEVICE FOR ACUTE PAIN MANAGEMENT BY SIMULTANEOUS SPINAL CORD ELECTRICAL STIMULATION AND DRUG INFUSION

BACKGROUND OF THE INVENTION

The invention relates generally to the use of a multi-lead electrode catheter positioned in the epidural space adjacent to the spinal cord to deliver electrical stimulation to a particular group of nerve fibers to control pain by blocking transmission of sensed pain along the nerve and/or spinal cord. More particularly, the invention relates to the use of a wide-range multi-lead electrode catheter having a drug infusion conduit for simultaneous, synergistic application of both electrical stimulation and analgesic medication in acute pain situations, whereby the levels of electrical stimulation and medication infusion needed to block pain sensation are significantly reduced below the levels required when either modality is administered independently. Proper positioning of the multi-lead electrode to provide analgesia for a desired body area covering three to four dermatomes and myotomes is accomplished without fluoroscopic assistance via patient paresthesia response alone.

The use of an epidural catheter for electrical spinal cord stimulation for the management of various conditions of chronic pain has been a proven technique for several decades, and it is in current, wide-spread use. Similarly, the use of an epidural catheter for drug infusion for acute pain management, not only for the relief of suffering, but for the modification of medical and surgical outcome, has been commonly practiced for many years. However, the clinical practice of employing an epidural catheter with the capability of electrical spinal cord stimulation in acute pain situations is unknown. This is because no stimulating epidural catheter currently exists which is practical for acute pain management. Because ease and speed of placement are essential for routine, acute pain therapy applications, the ability to place the catheter without fluoroscopic aid by any physician or nurse anesthetist facile with conventional percutaneous epidural catheter placement is mandatory. The capability of anatomically precise percutaneous placement of a stimulating epidural catheter by electrically stimulated paresthesias alone will greatly enlarge the applicability of the proven technique of electrical spinal cord stimulation for pain management, because severe acute pain states, such as post-operative pain and labor pain, are much more common than severe chronic pain states.

It is known to use local anesthetics and narcotics to control pain sensation in certain acute and chronic pain states by direct infusion of relatively large amounts of these drugs into the epidural space surrounding the spinal cord. This methodology has certain problems however, since the medication dosages required may be relatively large and since numerous significant side effects may occur which are directly proportional in incidence, prevalence and severity to the amount of infused medication. In chronic pain applications, the patients can build up resistance to the beneficial effects of epidural narcotics, necessitating progressively increasing narcotic dosages.

It is also known to moderate or alleviate chronic pain by electrical stimulation of the spinal cord via implantation of an electrode device in the epidural space of the spine. The electrode is positioned by laminectomy and direct visual assessment while the patient is under general anesthesia, or by percutaneous needle placement employing X-ray or fluoroscopic techniques with the patient under local anesthesia. Both methods of implantation require significant time and expense, and as such are impractical and thus not utilized in acute pain situations. positioning with the use of X-ray or fluoroscopy has the added detriment of exposing the patient and implantation team to radiation.

The known electrode devices are typically designed for long-term implantation for relief in chronic pain situations rather than short-term, acute pain situations, such as would be experienced during and after a surgical operation. In particular, the known electrode devices provide an anatomically limited range of stimulation, usually covering only the nerve fibers corresponding to one nerve or dermatome/myotome region, since the designed application is for relief of a particular or localized pain. Because of the limited distribution of the generated electrical field, these electrodes would not be suitable for desensitizing the number of nerve fibers associated with three to four dermatomes and myotomes involving a surgical incision, for example. The known electrode devices also do not provide for simultaneous delivery of drugs to the spinal area, and require fluoroscopic assistance for implantation.

It is an object of this invention to provide method and means for correct, rapid and relatively simple percutaneous insertion and positioning of the dual function epidural electrode catheter without requiring the use of fluoroscopy or general anesthesia by utilizing patient paresthesia response to electrical stimulation alone to determine when the epidural catheter is properly positioned for optimal pain desensitization. The broader electrical field of this device will allow for less precise anatomic placement and therefore this methodology will be employable by any operator qualified in the percutaneous placement of a conventional epidural catheter.

It is a further object of this invention to provide a method and a device for treatment of acute pain conditions by simultaneously administering both electrical stimulation and drug medication to the epidural space and spinal cord. This ability to simultaneously deliver dual modalities allows the level of each individual modality to be reduced below the level necessitated when either modality is independently used, the synergistic combination of the dual modalities providing the required level of analgesia while decreasing or eliminating the adverse side effects of each individual modality.

It is a further object of this invention to provide a method and a device for treatment of acute pain situations by administering electrical stimulation over a broad range of nerve fibers corresponding to at least three to four dermatomes and myotomes, the electrical field thus covering the area of a typical surgical incision and also allowing for less precise anatomic placement.

It is a further object to provide a method and means suitable for use with acute pain situations whereby the ease of implantation allows for its economical use in a variety of acute medical and surgical scenarios, such as perioperative pain, labor pain, acute nonsurgical pain, and limb or graft ischemia.

SUMMARY OF THE INVENTION

The invention is a device for management of acute pain comprising a multi-lead electrode catheter capable of producing a longitudinally elongated electrical field with the simultaneous ability to deliver analgesic medications, as well as the method encompassing the use of this device via percutaneous implantation in the epidural region of the spinal cord without fluoroscopic assistance. The electrode catheter is quickly and easily positioned in the epidural space adjacent to the patient's spinal cord under local anesthesia. Precise positioning to provide analgesia for the appropriate body region is accomplished by activating the electrodes and moving the catheter relative to the spinal cord in response to communication from the patient, who senses paresthesias (tingling or pricking sensations) in the body region corresponding to the particular nerves or nerve fibers being electrically stimulated. The electrode catheter stimulates a range of nerve fibers corresponding to at least three or four dermatomes and myotomes, a distance of approximately ten to fifteen centimeters, such that analgesia is provided for a broad anatomic region of the patient. A combination of electrical stimulation and infused medication, the applied amount of each being of lesser magnitude than would be required if either modality were employed independently, is then utilized to desensitize the anatomic region of the acute pain condition, such as a surgical operation or labor pain. This catheter is the first spinal cord stimulation catheter useful in acute pain management situations due to its ease of placement without fluoroscopy by physicians and nurse anesthetists familiar with the standard percutaneous epidural catheter placement technique, its wide elongated electrode field which covers a number of dermatome regions, and its ability to provide simultaneous electrical stimulation and medication infusion for synergy and side effect reduction.

In general, the process comprises the steps of anesthetizing the insertion area by local anesthetic infiltration and inserting the catheter needle into the epidural space of the spine. The multi-lead electrode catheter is then advanced through the needle into the epidural space using a bent-tipped steering stylet inserted through the drug delivery conduit. When the electrode catheter is positioned in the general location for stimulation of the desired nerve fibers, the electrical stimulation current is activated, providing analgesia in the body area dermatomes and myotomes corresponding to the nerve fibers being affected by the electrical field of the electrode catheter. As the patient is awake and responsive during the procedure, the operator can determine the affected area by communicating with the patient, who will experience paresthesias or tingling in the dermatomal and myotomal areas being electrically stimulated. The operator then accurately positions the electrode catheter along the spinal column by moving the electrode catheter until the patient indicates that he or she is experiencing paresthesias in the desired body area - for example, where the incision for an operation is to be made or in the region experiencing labor pain. Since the catheter may need to be advanced or retracted through the needle during positioning, the catheter preferably has an armored construction to resist shearing by the sharp bevel tip of the needle. The insertion needle and the steering stylet are then withdrawn, leaving only the electrode catheter in the patient. The electrode catheter is then taped in place and covered with sterile dressing. Finally, the electrode catheter is connected to an infusion pump for delivery of the analgesic medication. During the acute pain condition, both electrical stimulation and medication infusion are simultaneously utilized, the combined synergistic effect of both modalities lessening the total amount of electrical stimulation and infused medication required to maintain the necessary state of analgesia. The analgesic medication may be either continuously or bolus infused, and the electrical stimulation controlled in known manner with regard to such variables as current, voltage, waveform, and length of electrical field band. One or more of the electrical stimulator variables may have the option of being patient-variable within physician determined ranges.

DETAILED DESCRIPTION OF THE INVENTION

Figure 2:
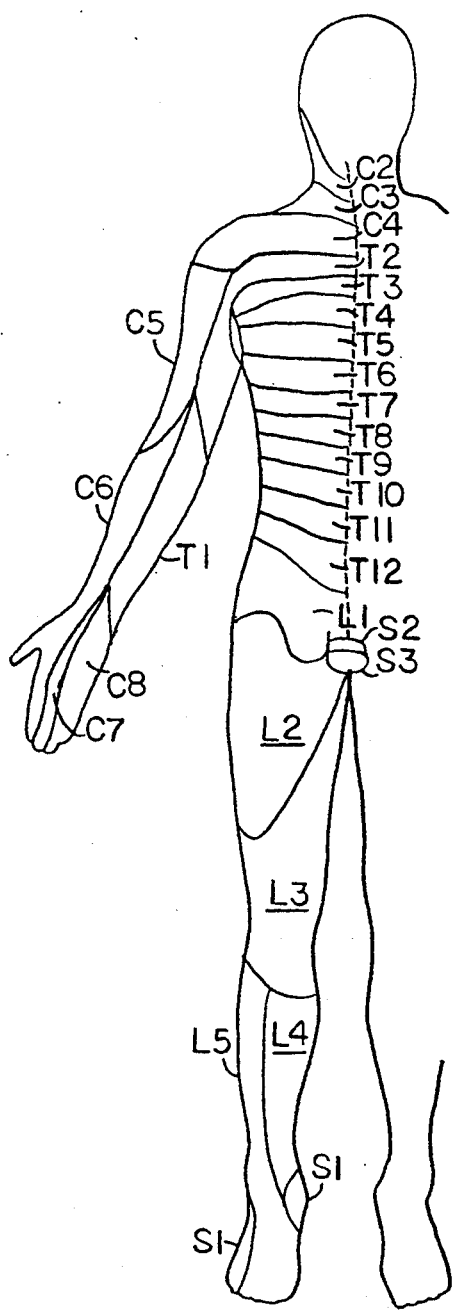
FIG. 2 is an illustration of the front or ventral aspect of the human body showing the dermatome and underlying myotome regions and the corresponding spinal location of the nerves.
Figure 3:
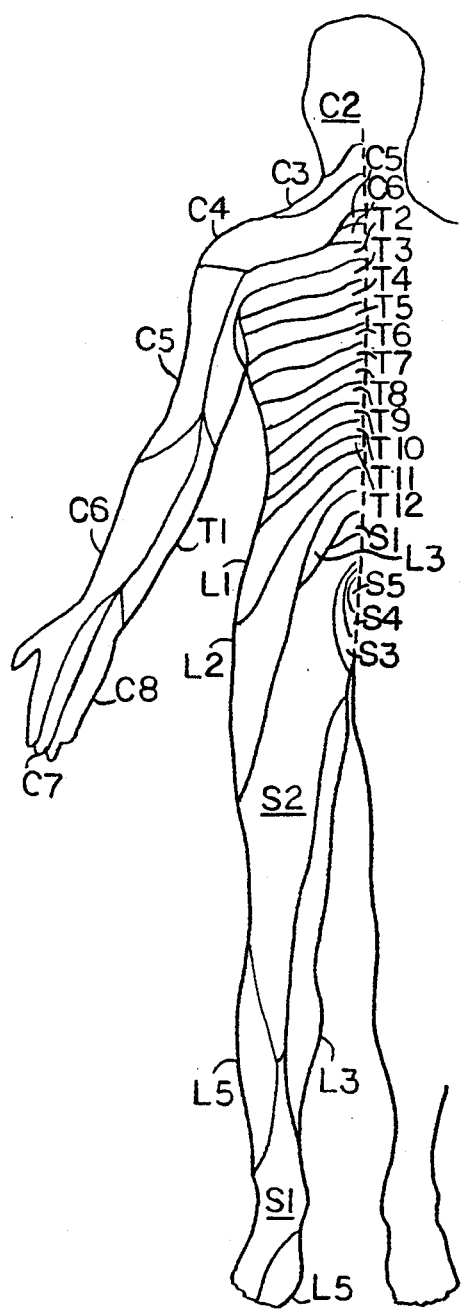
FIG. 3 is an illustration of the rear or dorsal aspect of the human body showing the dermatome and underlying myotome regions and the corresponding spinal location of the nerves.

The invention is a method and means for providing analgesia for a body region comprising plural dermatomes and myotomes in acute pain scenarios, comprising the use of a multi-lead electrode catheter having a longitudinally extended field of electrical stimulation, placed without fluoroscopic assistance, capable of simultaneously electrically stimulating the nerves or spinal cord associated with three to four body dermatomes and myotomes as well as simultaneously delivering an infusion of analgesic medication. A dermatome is an area of skin innervated by the nerve fibers arising from a specific vertebral level of the spinal cord. A myotome is a corresponding group of muscles innervated by the nerve fibers arising from a specific vertebral level of the spinal cord. As seen in FIGS. 2 and 3, individual dermatomes and their related myotomes, indicated by C2 through C8, T2 through T12, L1 through L5, and S2 through S3, can cover relatively broad or narrow regions of the body. The nerves corresponding to a particular dermatome and myotome stem from a relatively localized position on the spinal column. In order to provide analgesia for a single particular dermatome and myotome region, it is known to position an electrode catheter at the corresponding vertebral level of the spinal cord. The application of electrical current then blocks the transmission of pain signals from the nerves of the dermatome and myotome to the brain. It is also known to provide analgesia for a particular dermatome and myotome by infusing analgesic medications into the epidural space of the spinal cord corresponding to the anatomic nerve locus of the desired dermatome and myotome.

Figure 1:
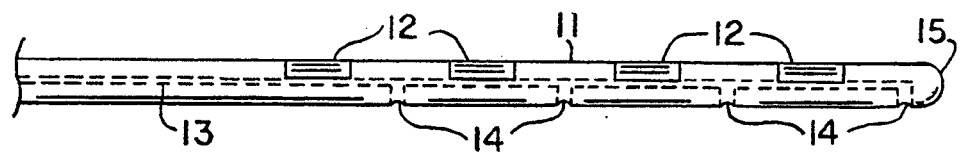
FIG. 1 is a side view of the insertable portion of the electrode catheter having both electrode leads and a drug delivery conduit.

The device of the invention is an electrode catheter capable of delivering electrical stimulation and delivering infused medications in the known manner, but having an elongated range of stimulation and infusion which is able to provide analgesia for at least three to four contiguous dermatomes and myotomes by simultaneously electrically stimulating and infusing medication to the nerve fibers along the spinal cord corresponding to these three to four dermatomes and myotomes. The design and construction of the catheter conforms generally to those known in the art, including mechanisms and means for connection to drug infusion devices and mechanisms and means for connection to electrical current supply devices to deliver controlled electrical stimulation, except as to the elongated anatomic range of stimulation covering three to four dermatome and myotome regions and the simultaneous ability to deliver analgesic medication by infusion. As seen in FIG. 1, the device comprises a plurality of electrodes or electrical leads 12 positioned along the length of the electrode carrying portion 11 at the insertion end 15 of the catheter. The leads 12 must cover a distance of at least ten centimeters in order to provide stimulation over at least three to four contiguous dermatome and myotome regions. In the preferred embodiment, the leads 12 will electrically stimulate a longitudinal distance of from ten to fifteen centimeters. In addition to the electrical leads 12, the catheter also comprises conduit means 13 for delivery of analgesic medication. Conduit 13 has at least one but preferably a plural number of openings 14 longitudinally spaced along the electrode carrying portion 11 which allow medication to be pumped through the catheter in the standard manner and infused directly to the desired location of the epidural space overlying the spinal cord. The conduit 13 also acts as the conduit for insertion of a steering stylet to precisely guide and position the catheter after initial insertion. Upon achievement of the proper position within the epidural space relative to the nerve fibers corresponding to the desired dermatomes and myotomes, the steering stylet is removed and the conduit 13 becomes the means for drug infusion to the epidural space. The electrode catheter, since it is designed for short-term acute use, may be constructed of less costly materials and the overall structural components may be designed to less rigorous standards than those currently in use for long-term, permanent implantation in chronic pain situations, thus lowering the cost of the device.

The electrode catheter described above can be used in acute pain situations, such as would be encountered during and after a surgical operation or during labor and childbirth. As such, the method of insertion, positioning and the pain relief mechanism is crucial. The method of the invention comprises in general the steps of inserting the electrode catheter into the epidural space of the spinal cord, accurately positioning the electrode catheter for proper analgesia solely by response to paresthesia indications communicated by the patient to the operator, and supplying a simultaneous dual modality of pain relief composed of both electrical stimulation and infusion of analgesic medication.

To insert the electrode catheter, the patient is placed in either the sitting, prone or lateral decubitus position, whichever provides the best accessibility to the spinal cord for the operator. The insertion site is prepared with a cleansing aseptic solution and the area draped with sterile drapes. Strict aseptic technique is utilized. Local anesthesia is administered and the needle is inserted into the epidural space via a vertebral interspace caudad to, or lower than, the spinal cord level to be stimulated. The insertion needle is preferably a Weiss-modified Tuohy-schliff needle with stylet which possesses a wider than usual needle bevel opening to minimize the risk of catheter shear. The electrode catheter is threaded through the needle into the epidural space. The catheter is advanced cephalad, or upward, in the epidural space until the electrical leads are approximately positioned at the desired anatomic location to stimulate the spinal cord and appropriate nerves corresponding to the desired dermatomes and myotomes to be affected. The electrode catheter is connected in known manner to an electrical stimulator device and electrical stimulation is activated at a relatively low current and voltage which is sufficient to produce paresthesias in the patient. A paresthesia is the perception of tingling or "pins and needles" in the dermatomes and myotomes whose innervating nerve fibers are being stimulated by the electrical leads of the catheter. Since the electrode catheter has a wide anatomic distribution of electrical stimulation due to the relatively elongated spread of the electrical leads and resulting electrical field, three to four dermatomes and myotomes will be affected by this single device. As the patient is conscious and the placement procedure is performed only under local anesthesia, the operator can determine if the appropriate dermatomes and myotomes are being affected by the electrical stimulation through vocal communication with the patient. Axial and lateral positioning of the electrode catheter in the epidural space along the spinal cord using the steering stylet inserted through the medication infusion conduit, as guided by the elicited patient paresthesias, will result in the sufficiently precise anatomic placement of the catheter necessary to provide analgesia to the desired dermatomes and myotomes. Once this is achieved, the stylet is withdrawn through the conduit and the needle is removed from the patient. The catheter is taped securely in place. The insertion site is covered with a sterile occlusive dressing and the catheter is connected to a medication infusion pump in a conventional manner.

To provide analgesia in the desired dermatomes and myotomes, a combination of infused medication and electrical stimulation is employed. This combined modality allows the operator to alleviate or reduce some or all of the disadvantages of individual utilization of electrical stimulation or medication infusion for analgesia. The drawback of electrical stimulation when used as a single modality for pain management is that many patients find the paresthesia effects painful or annoying, especially if large voltages or currents are required to sufficiently desensitize the dermatome and myotome. The adverse side effects of epidural medications include nausea, vomiting, urinary retention, sedation and respiratory depression associated with narcotics; and motor/sensory deficits associated with local anesthetics. Providing a device which enables the physician to simultaneously apply both electrical stimulation and infusion of medication allows the physician to take advantage of the synergistic combination of modalities and thus utilize lesser amounts of each while still providing the necessary level of analgesia, thus decreasing the risk of adverse and toxic side effects from each component modality.

As an example, the method and device can be used for an acute pain scenario such as the removal of a gall bladder. With reference to FIG. 2, it is seen that analgesia must be provided for dermatomes and underlying myotomes T7 through T10 in order to cover the necessary surgical incision. By inserting and positioning the electrode catheter in the epidural region of the spinal cord corresponding to the nerve fiber positions of dermatomes and myotomes T7, T8, T9 and T10, via the methodology of patient response described above, the physician is able to apply electrical stimulation and drug infusion to desensitize the required dermatomes and myotomes. The insertion and proper positioning of the electrode catheter is quickly and easily accomplished without assistance of fluoroscopy. As another example, to perform knee surgery, the electrode catheter would be positioned along the vertebral region encompassing the nerves for dermatomes and myotomes L2 through L5.

Because ease and speed of placement are essential for routine, acute pain therapy applications, the ability to place the catheter without fluoroscopic aid is mandatory. Anatomically precise percutaneous placement solely by electrically stimulated paresthesias enables the physician to utilize this methodology in such applications. The importance of acute pain management, not only for the relief of suffering, but for the modification of medical and surgical outcomes, is becoming widely acknowledged.

It is understood that the above examples are by way of illustration only and that equivalents and substitutions may be obvious to those skilled in the art. The full scope and definition of the invention therefore is to be as set forth in the following claims.

I claim:

1. A method for treatment of acute pain in a patient by providing analgesia for at least three contiguous dermatome and myotome regions by the combined application of electrical stimulation and infused medication to the nerve fibers and portion of the spinal cord associated with said dermatome and myotome regions, comprising the steps of:

(A) providing an electrode catheter adapted for insertion into the epidural region of the spinal cord having both conduit means to deliver analgesic medications and a plurality of electrical leads capable of providing electrical stimulation to nerve fibers and a portion of the spinal cord over a longitudinal distance of at least ten centimeters;

(B) providing means to insert said electrode catheter percutaneously into the epidural region of the spinal cord adjacent to said nerve fibers and said portion of the spinal cord;

(C) inserting said electrode catheter into said epidural region without the aid of fluoroscopy;

(D) activating said electrical stimulation to stimulate said nerve fibers and said portion of the spinal cord to create paresthesias in corresponding dermatome and myotome regions;

(E) communicating with the patient to determine which dermatome and myotome regions are experiencing paresthesias;

(F) positioning said electrode catheter within said epidural region to stimulate said nerve fibers and said portion of the spinal cord associated with the particular dermatome and myotome regions to be provided analgesia through continued communication with the patient as to which dermatome and myotome regions are experiencing paresthesias;

(F) providing analgesia to said particular dermatome and myotome regions by simultaneous application of electrical stimulation and infusion of analgesic medication to said nerve fibers and said portion of the spinal cord.

2. A method for treatment of acute pain in a patient by providing analgesia to at least three contiguous dermatome and myotome regions by the combined application of electrical stimulation and infused medication to the nerve fibers and portion of the spinal cord associated with said dermatome and myotome regions, comprising the steps of:

(A) providing an electrode catheter adapted for insertion into the epidural region of the spinal cord having both conduit means to deliver analgesic medications and a plurality of electrical leads capable of providing electrical stimulation to nerve fibers and a portion of the spinal cord over a longitudinal distance sufficient to stimulate the nerve fibers corresponding to at least three dermatome and myotome regions;

(B) providing means to insert said electrode catheter percutaneously into the epidural region of the spinal cord adjacent to said nerve fibers and said portion of the spinal cord;

(C) inserting said electrode catheter into said epidural region without the aid of fluoroscopy;

(D) activating said electrical stimulation to stimulate said nerve fibers and said portion of the spinal cord to create paresthesias in corresponding dermatome and myotome regions;

(E) communicating with the patient to determine which dermatome and myotome regions are experiencing paresthesias;

(F) positioning said electrode catheter within said epidural region to stimulate said nerve fibers and said portion of the spinal cord associated with the particular dermatome and myotome regions to be provided analgesia through continued communication with the patient as to which dermatome and myotome regions are experiencing paresthesias;

(F) providing analgesia to said particular dermatome and myotome regions by simultaneous application of electrical stimulation and infusion of analgesic medication to said nerve fibers and said portion of the spinal cord.

* * * * *